(12) United States Patent
Parks

(10) Patent No.: US 9,220,485 B2
(45) Date of Patent: Dec. 29, 2015

(54) TISSUE COLLECTION AND SEPARATION DEVICE

(71) Applicant: EndoChoice, Inc., Alpharetta, GA (US)

(72) Inventor: William Parks, Lawrenceville, GA (US)

(73) Assignee: EndoChoice, Inc., Alpharetta, GA (US)

( * ) Notice: Subject to any disclaimer, the term of this patent is extended or adjusted under 35 U.S.C. 154(b) by 202 days.

(21) Appl. No.: 13/662,064

(22) Filed: Oct. 26, 2012

(65) Prior Publication Data

US 2014/0121560 A1    May 1, 2014

Related U.S. Application Data

(63) Continuation of application No. 13/220,425, filed on Aug. 29, 2011, now Pat. No. 8,465,439.

(60) Provisional application No. 61/377,944, filed on Aug. 28, 2010.

(51) Int. Cl.
*A61B 10/00* (2006.01)
*A61B 10/02* (2006.01)
*A61M 1/00* (2006.01)

(52) U.S. Cl.
CPC .......... *A61B 10/0283* (2013.01); *A61M 1/0056* (2013.01); *A61B 10/0045* (2013.01); *A61B 10/0096* (2013.01)

(58) Field of Classification Search
CPC ................. A61B 10/0096; A61B 2010/0225; A61M 1/0056; A61M 1/0001; B01D 29/0097; B01D 29/01
USPC .......................... 600/562, 575; 604/317, 319
See application file for complete search history.

(56) References Cited

U.S. PATENT DOCUMENTS

| | | | |
|---|---|---|---|
| 3,719,086 A | 3/1973 | Bannister | |
| 3,994,297 A | 11/1976 | Kopf | |
| 4,439,319 A * | 3/1984 | Rock | 210/238 |
| 4,443,220 A * | 4/1984 | Hauer et al. | 604/408 |
| 4,643,197 A * | 2/1987 | Greene et al. | 600/575 |
| 4,852,560 A * | 8/1989 | Hermann et al. | 600/575 |
| 5,526,822 A | 6/1996 | Burbank | |
| 5,532,168 A * | 7/1996 | Marantz | 436/176 |
| 5,624,418 A * | 4/1997 | Shepard | 604/319 |

(Continued)

FOREIGN PATENT DOCUMENTS

WO     2004075728 A2    9/2004

OTHER PUBLICATIONS

ConMed Endoscopic Technologies, Optimizer Polyp Trap, Product Specification Sheet, ConMed Corporation, Apr. 2007, Control #12739 Rev B.

(Continued)

*Primary Examiner* — Sean Dougherty
(74) *Attorney, Agent, or Firm* — Novel IP

(57) ABSTRACT

An improved tissue specimen trapping device for collecting and separating solid particles and materials from body fluids has a porous separator that rests on a shelf-like annular ledge between upper and lower portions of the tissue collection container. At least one tissue collection basket removably disposed in the tissue collection container above the separator shelf has a porous bottom surface to filter tissue specimens from body fluids and has downward projections to the tissue collection basket above the separator shelf to create a space therebetween.

9 Claims, 5 Drawing Sheets

(56) References Cited

U.S. PATENT DOCUMENTS

| | | | |
|---|---|---|---|
| 5,649,547 A | 7/1997 | Ritchart | |
| 5,769,086 A | 6/1998 | Ritchart | |
| 5,775,333 A | 7/1998 | Burbank | |
| 5,817,032 A * | 10/1998 | Williamson et al. | 600/562 |
| 5,873,967 A | 2/1999 | Clark | |
| 5,928,164 A | 7/1999 | Burbank | |
| 5,964,716 A | 10/1999 | Gregoire | |
| 5,980,469 A | 11/1999 | Burbank | |
| 6,007,497 A | 12/1999 | Huitema | |
| 6,017,316 A | 1/2000 | Ritchart | |
| 6,042,593 A | 3/2000 | Storz | |
| 6,077,230 A | 6/2000 | Gregoire | |
| 6,086,544 A | 7/2000 | Hibner | |
| 6,120,462 A | 9/2000 | Hibner | |
| 6,228,055 B1 | 5/2001 | Foerster | |
| 6,231,522 B1 | 5/2001 | Voegele | |
| 6,273,862 B1 | 8/2001 | Privitera | |
| 6,299,763 B1 * | 10/2001 | Ashman | 210/94 |
| 6,428,486 B2 | 8/2002 | Ritchart | |
| 6,436,054 B1 | 8/2002 | Viola | |
| 6,485,436 B1 | 11/2002 | Truckai | |
| 6,488,636 B2 | 12/2002 | Bryan | |
| 6,638,235 B2 | 10/2003 | Miller | |
| 7,025,732 B2 | 4/2006 | Thompson | |
| 7,156,814 B1 * | 1/2007 | Williamson et al. | 600/562 |
| 7,189,206 B2 | 3/2007 | Quick | |
| 7,244,236 B2 * | 7/2007 | Merkle | 600/575 |
| 7,276,032 B2 | 10/2007 | Hibner | |
| 7,278,991 B2 | 10/2007 | Morris | |
| 7,758,515 B2 * | 7/2010 | Hibner | 600/566 |
| 8,128,578 B2 * | 3/2012 | Peltier | 600/569 |
| 8,465,439 B2 * | 6/2013 | Parks | 600/562 |
| 2003/0086830 A1 * | 5/2003 | Haywood et al. | 422/102 |
| 2003/0125639 A1 | 7/2003 | Fisher | |
| 2003/0132249 A1 | 7/2003 | Romano | |
| 2003/0199753 A1 | 10/2003 | Hibner | |
| 2003/0199787 A1 | 10/2003 | Schwindt | |
| 2004/0153003 A1 | 8/2004 | Cicenas | |
| 2004/0167428 A1 | 8/2004 | Quick | |
| 2005/0065453 A1 | 3/2005 | Shabaz | |
| 2005/0203439 A1 | 9/2005 | Heske | |
| 2005/0215921 A1 | 9/2005 | Hibner | |
| 2006/0074342 A1 | 4/2006 | Hibner | |
| 2006/0074343 A1 | 4/2006 | Hibner | |
| 2006/0074344 A1 | 4/2006 | Hibner | |
| 2006/0074345 A1 | 4/2006 | Hibner | |
| 2006/0260994 A1 | 11/2006 | Mark | |
| 2007/0032741 A1 | 2/2007 | Hibner | |
| 2007/0032743 A1 | 2/2007 | Hibner | |
| 2007/0191731 A1 * | 8/2007 | Kaye et al. | 600/562 |
| 2007/0239067 A1 | 10/2007 | Hibner | |
| 2007/0255174 A1 | 11/2007 | Hibner | |

OTHER PUBLICATIONS

Olympus, Suction Polyp Trap, Product Specification Sheet, Cat. No. H334, 2010.

* cited by examiner

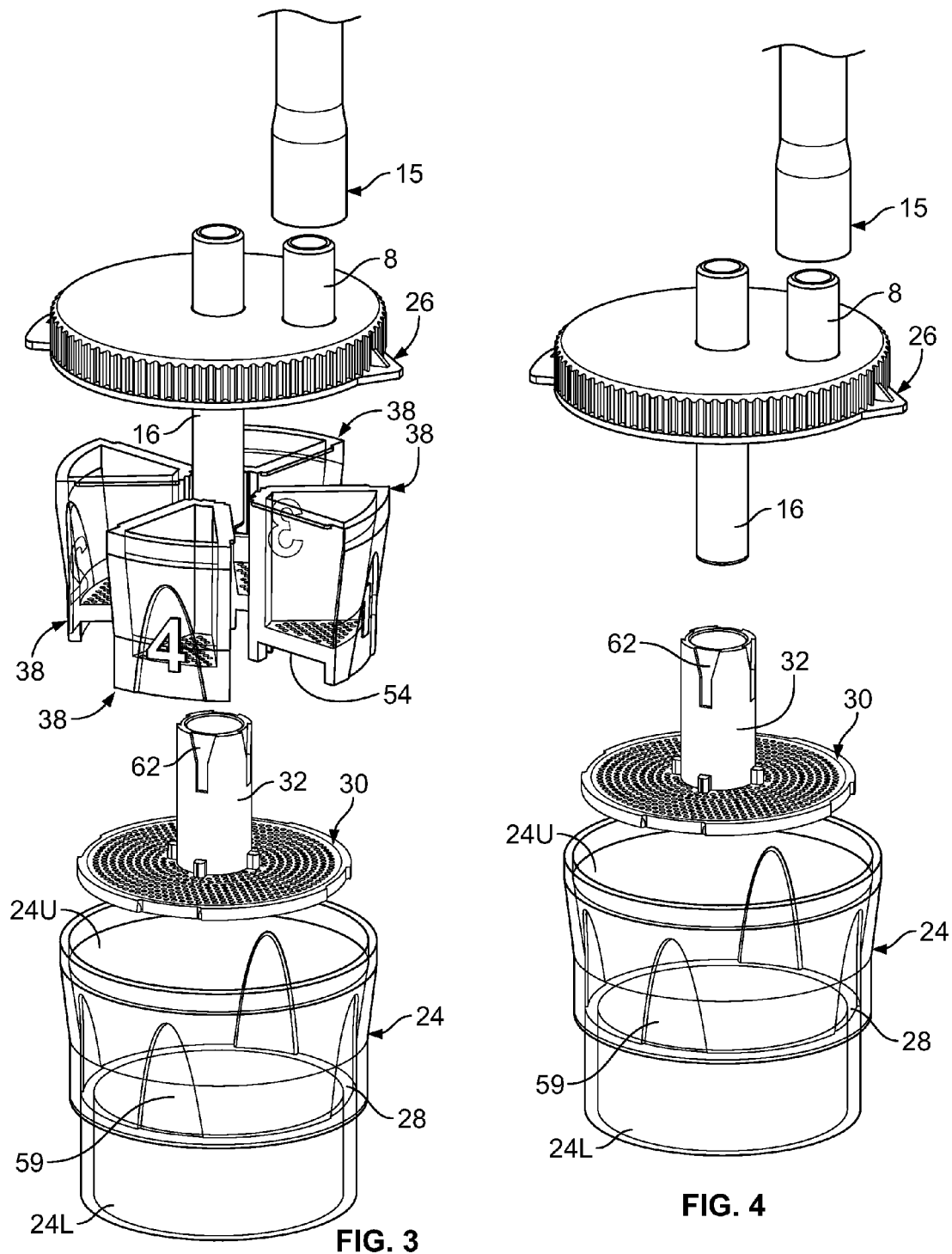

TISSUE COLLECTION AND SEPARATION DEVICE

CROSS-REFERENCE

The present specification is a continuation of U.S. patent application Ser. No. 13/220,425, filed on Aug. 29, 2011.

FIELD

The present specification discloses a tissue specimen collection device for collecting fluid-borne tissue specimens from a body. More specifically, the present specification discloses tissue specimen collection and separation devices for use within a suction collection and drainage apparatus and with a suction source to withdraw and separate tissue specimens from body fluids of a patient.

BACKGROUND

It is often desirable to isolate tissue specimen from the body of a human or animal patient for pathological analysis. Many times, however, the tissue specimen is not easily obtained from the patient, either because of where it is situated or because it is present within a body fluid and, therefore, difficult to isolate. A common method for isolating from the patient a specimen of tissue that is present within a body fluid is by removing a sample of the body fluid from the patient using suction, so as to collect a sample of the fluid containing the desired solid tissue specimen, and by straining the fluid sample using a straining medium to isolate the tissue specimen.

Devices have been developed to create suction and provide drainage of the fluid with the tissue specimen from the human or animal patient's body. Some such devices may include a collection container or canister with a liner or strainer operatively coupled to a vacuum source. Some such devices may also include a tissue specimen trap that is connected between the patient and the collection container in order to separate the tissue specimen from the body fluid.

For example, in U.S. Pat. No. 4,643,197 (Greene et al.), a tissue collection and separation apparatus has separate fluid collection and tissue specimen trap containers. A first tube connects the fluid collection container to a source of suction, a second tube connects the fluid collection container to the specimen trap container, and a third tube connects the specimen trap container to an endoscope that aspirates the tissue specimen and fluid from the patient and transmits them to the specimen trap container. A filter is supported across the specimen trap container to selectively receive and collect the tissue specimen from the body fluid or permit passage therethrough of body fluids, when suction is applied to the apparatus.

In U.S. Pat. No. 5,624,418 (Shepard), the tissue collection and separation apparatus also has separate fluid and tissue collection containers, the fluid collection container coupled to a suction source and the tissue collection container coupled between the patient and the fluid collection container. The tissue collection container has at least one tissue collection basket removably disposed therein above a fluid collection zone and has a separator bottom to separate the tissue specimens from the body fluids. When body fluids and tissue specimen from the patient are received in the tissue collection basket, the tissue specimens are retained therein for subsequent removal and the body fluids are allowed to flow to the fluid collection zone for collection and removal to the fluid collection container.

U.S. Pat. No. 7,244,236 (Merkle) teaches a specimen trapping container within a tissue collection and separation apparatus, having at least a container forming a chamber with a porous strainer affixed across the chamber to provide fluidic communication between upper and lower chamber portions. A tube coupled to the patient passes through the cap, and another tube coupled to a suction source a fluid collection container extends through the cap and through the strainer into the lower portion. The cap is rotatable with respect to the container to form communication between one of several specimen compartments and the one tube connection passage for collection of an independent specimen.

It is desirable to provide a tissue specimen trapping device to be used in medical procedures to enable collection and separation of solid particles (e.g., tissue specimen) from within body fluids suctioned from a patient.

SUMMARY

It is one object of this invention to provide an improved tissue specimen trapping device for collecting and separating solid particles and materials from within body fluids suctioned from a patient.

It is another object of this invention to provide an improved tissue specimen trapping device for retrieving or collecting multiple independent specimens from within body fluids suctioned from a patient.

In accordance with the above and other objects of this invention, an improved tissue specimen trapping device for collecting and separating solid particles and materials from body fluids is to be used in combination with a fluid collection container and to be operatively coupled to a suction source that withdraws the body fluid from a patient. The tissue specimen trapping device comprises a tissue collection container operatively coupled between the patient and the fluid collection container so as to trap the tissue specimens therein.

In one embodiment, the tissue specimen collection device has a separator shelf that divides the tissue collection container into upper and lower portions thereof and that has holes or pores formed therethrough to provide fluid communication between the upper portion and the lower portion. The separator shelf filters tissue specimens from the body fluids as body fluids pass through any portion of the separator shelf. In one embodiment, the separator shelf has an annular post extending upward towards the cover of the tissue collection container.

The cover of the tissue collection container has a fluid/tissue inlet port formed therethrough and a first tube connection mounted to the cover and forming a passage therethrough, such that the first tube is in fluid communication with the upper portion of the tissue collection container. The distal end of this first tube is connected to an endoscope that collects body fluids and tissue specimen from a patient and transmits them the tissue specimen collection device. The cover also has a fluid outlet port formed therethrough to which a second tube operatively connects the tissue collection container for fluid communication therebetween. In one embodiment, the cover has an extension tube that extends downward from the inside surface of the cover through the separator shelf into the lower portion of the tissue collection container, forming a passage in fluid communication with the lower portion of the tissue collection container. In another embodiment, the second tube that connects the tissue collection container to the fluid connection container extends through the cover and through the tissue collection container at central locations of each, and into the lower region of the tissue collection container.

The tissue specimen collection device has at least one tissue collection basket removably disposed in the tissue collection container above the separator shelf. In one embodiment, the lower surface of each tissue collection basket has holes or fluid flow apertures formed therethrough to filter or retain within that tissue collection basket tissue specimens from the body fluids for subsequent removal therefrom, while allowing body fluids to pass therethrough.

In one embodiment, the outer wall of the tissue collection container is substantially cylindrically shaped, and the outside arcuate wall of each tissue collection basket has a corresponding arcuate shape. In one embodiment, the side walls of each tissue collection basket removably disposed in the tissue collection container are oriented substantially radially with respect to the tissue collection container. Preferably, the side walls of each tissue collection basket extend from a top surface of the separator shelf to the top of the tissue collection container, abutting the underside of the cover. When the cover is rotated with respect to the tissue collection container, communication between the first tube and one of the tissue collection baskets can be selected so as to choose which tissue collection basket will receive the body fluid being evacuated from the patient's body.

The tissue collection basket bottom surface and the tissue specimen trapping device separator shelf together provide redundant separation of tissue specimen from body fluids passing therethrough. In one embodiment, each tissue collection basket also has projections, e.g., feet, that protrude downward from the bottom of the tissue collection basket, so as to raise the bottom surface filter of the tissue collection basket slightly above the separator shelf and to create a space therebetween, in order to prevent clogging of the respective filter holes of the tissue collection basket and of the separator shelf.

In one embodiment, the tissue specimen collection device further includes a basket positioning means to ensure that each tissue collection basket is properly and securely positioned in a correct tissue collection basket zone. Specifically, the basket positioning means prevents a collection basket from being placed at an incorrect location within the tissue collection container. In addition, the basket positioning means allows the tissue collection basket to be retained in such position, once inserted, by preventing it from moving (or from being moved) circumferentially with respect to the cylindrically-shaped tissue collection container.

In certain embodiments, the basket positioning means comprises a group of cooperating projections and recesses on the inside circumferential wall of the tissue collection container and on the outside arcuate walls of the tissue collection baskets, and/or on the outer surface of the central column within the tissue collection container and on the inner arcuate walls of the tissue collection baskets. In one embodiment, the basket positioning means comprises a group of projections on the inside circumferential wall of the tissue collection container and a corresponding group of recesses on the outside arcuate walls of each tissue collection basket. In another embodiment, the outer surface of the central column within the tissue collection container has a slight recess in its upper portion, and each tissue collection basket has a corresponding projection on the outer surface of the inner arcuate wall of the tissue collection basket adjacent to the central post. The cooperating projections and recesses cooperate to ensure that the tissue collection basket is placed into, and retained in, the tissue collection container at a collection zone about the central column.

The tissue specimen collection device also includes a tactile alignment means to provide a tactile indication that the first tube, namely the fluid/tissue inlet port, is aligned with respect to a tissue collection basket within the tissue collection container. In one embodiment, the underside of the cover is provided with at least one projection that rubs against the upper edge of the side walls of the tissue collection baskets as the projection passes over the upper edges of the side walls of each tissue collection basket when the cover is rotated on the tissue collection container. The bumping feeling that the user feels when the projection rubs against the upper edges of the side walls of the tissue collection baskets provides the user with a tactile indication of the rotation of the cover with respect to the tissue collection container and the position of the fluid/tissue inlet port with respect to a tissue collection basket as an indication of whether the fluid/tissue inlet port is properly aligned with respect to the tissue collection container.

The cover can be rotated to align the first tube with a first tissue collection basket, so as to allow body fluids and tissue from the patient to flow into the first tissue collection basket when suction is applied to the tissue specimen collection device. The body fluids flow from the first tube through the holes at the bottom of the first tissue collection basket and through the holes in the separator shelf into the lower portion of the tissue collection container, while the tissue specimen are retained within that first tissue collection basket. The cover may then again be rotated to align the first tube with a second tissue collection basket so as to allow body fluids and tissue from the patient to flow into the second tissue collection basket when suction is applied to the tissue specimen collection device. The body fluids flow through the filter holes at the bottom of the second tissue collection basket and through the holes in the separator shelf into the lower portion of the tissue collection container, while the tissue specimen are retained in the second tissue collection basket.

The present invention will be better understood by reference to the following detailed discussion of specific embodiments and the attached figures, which illustrate and exemplify such embodiments.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which:

FIG. 3 shows an exploded perspective view of the tissue specimen collection device;

FIG. 4 shows an exploded perspective view of the tissue specimen collection device without tissue collection baskets;

DETAILED DESCRIPTION

The following preferred embodiments as exemplified by the drawings are illustrative of the invention and are not intended to limit the invention as encompassed by the claims of this application.

Figure 1:
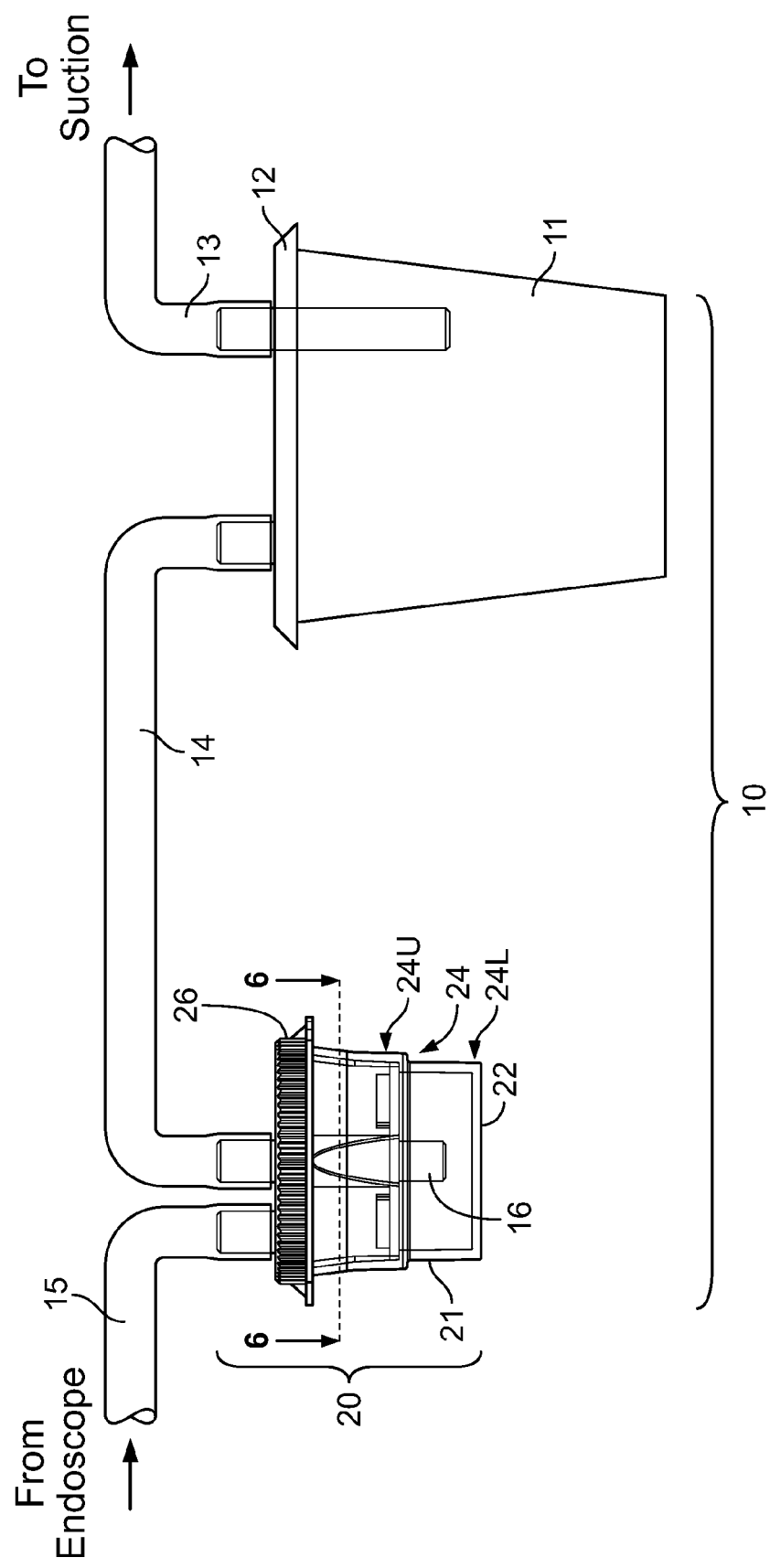
FIG. 1 shows a side view of the collection and separation device of the present invention in combination with a fluid collection container.
Figure 2A:
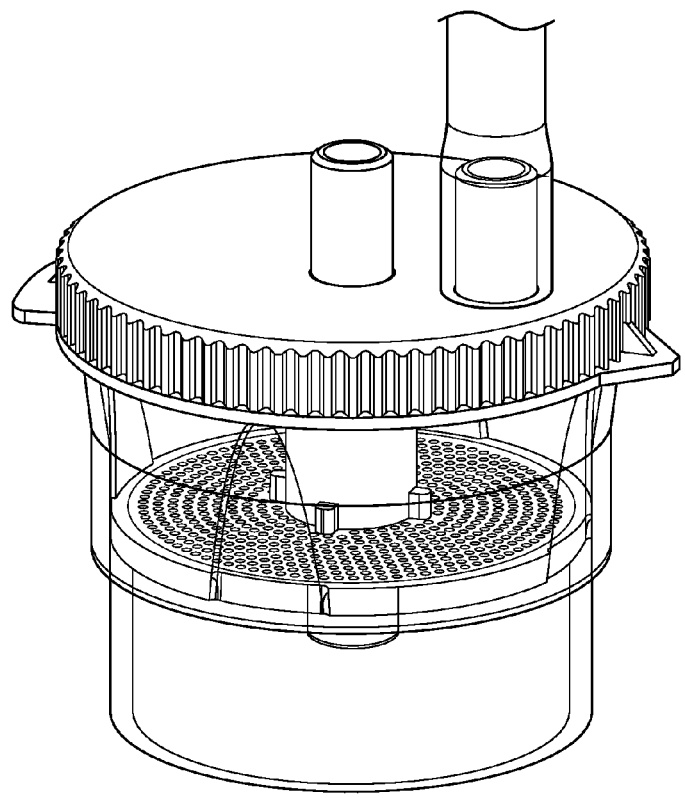
FIGS. 2A and 2B show perspective views of the tissue specimen collection device of the present invention without and with collection baskets situated therein, respectively.
Figure 2B:
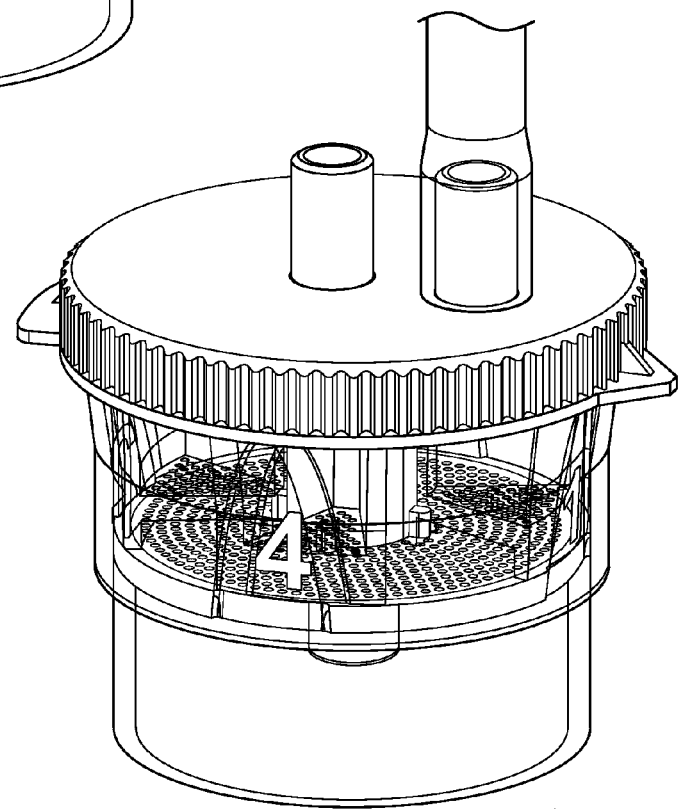

Referring to the drawings, FIG. 1 shows a suction collection and drainage apparatus 10 including a fluid collection container 11 and cover 12, through which suction tube 13 extends to provide communication between the interior of fluid collection container 11 and a source of suction (not shown). Apparatus 10 also includes a tissue specimen collection device 20 for collecting tissue specimens, having a separate second container 24 and a cover 26 that can be removably and rotatably affixed thereto. In some embodiments, cover 26 may be attached to container 24 by friction-fit or screw on, but is preferably attached by snap-on in a manner that permits rotational movement relative to one another. In a preferred embodiment, cover 26 is press-fitted onto container 24, as shown in FIG. 2, so as to create a substantially airtight seal.

As shown in FIG. 1, fluid tube 14 connects and provides fluid communication between tissue specimen collection device 20 and fluid collection container 11, with one end of tube 14 being secured to or extending through a suitable fluid outlet port in cover 26 of fluid collection container 21 and the opposite end of fluid tube 14 being secured to or extending through a suitable fluid inlet port in cover 12 of tissue collection container 11. The inlet and outlet ports are positioned such that the ends of fluid tube 14 pass through openings provided in the respective covers 26 and 12.

In one embodiment, the fluid outlet port formed through cover 26 of tissue collection container 24 allows the proximal end of fluid tube 14 to be passed through cover 26, such that fluid tube 14 is in fluid communication with the lower portion of the tissue collection container. In another embodiment, as shown in FIGS. 3 and 4, cover 26 has an extension tube 16 that extends downward from the inside surface thereof and into the lower portion of the tissue collection container 24, and forms a passage that puts fluid tube 14 in fluid communication with the lower portion of the tissue collection container 24. In either embodiment, the inserted end of fluid tube 14 or of extension tube 16 extends far into tissue collection container 24, terminating short of the bottom wall 22. In certain embodiments, fluid tube 14 is positioned through an opening provided in cover 26, such that cover 26 is rotatable with respect to the tissue collection container 24 about an axis that is incidental with the proximal end of fluid tube 14.

Tissue tube 15 connects tissue collection container 24 to an endoscope (not shown) via inlet end of tissue tube 15 that extends through a tube connection and fluid/tissue inlet port 8 in cover 26 to form a passage through cover 26, such that tissue tube 15 is in fluid communication with the upper portion of tissue collection container 24. The distal end of tissue tube 15 is connected to an endoscope that collects body fluids and tissue specimen from a patient and transmits them to tissue specimen collection device 20.

The parts of suction collection and drainage apparatus 10 may be made of such materials as are known in the art, such as those that are lightweight, durable and inexpensive, such as plastic.

In one embodiment, the tissue collection container 24 is substantially cylindrically shaped. As shown in FIGS. 1-6, the tissue collection container 24 comprises a substantially cylindrical side wall 21 and a circular bottom wall 22 formed on the lower periphery thereof. In one embodiment, the cylindrical side wall 24 has an upper portion with a first diameter and a lower portion with a second diameter, wherein the second diameter may be smaller than the first diameter. In one embodiment, the structural change in diameter of the cylindrical side wall 24 is abrupt so as to form in the side wall 24 of the tissue collection container a ledge-like indentation 28 that may assist in retaining a separator shelf in its position within the tissue collection container in a manner hereinbelow described.

In one embodiment, as best shown in FIGS. 3 and 4, the tissue specimen collection device has a separator shelf 30 that divides the tissue collection container 24 into an upper portion 24U and a lower portion 24L thereof. The separator shelf 30 can be supported within the tissue collection container 24 in any manner known. In one embodiment, the separator shelf 30 is supported by the ledge-like indentation 28 in the cylindrical side wall 24 of the tissue collection container 24, which separator shelf 30 functions as a seat for the separator shelf 30. In a preferred embodiment, the separator shelf 30 has holes or pores formed therethrough in the form of a filter to allow fluid communication between the upper portion 24U and the lower portion 24L of the tissue collection container 24. The separator shelf 30 filters tissue specimens from the body fluids as the body fluids pass through any portion of the separator shelf 30. In one embodiment, the separator shelf 30 has an annular post 32 extending upward towards the cover 26 of the tissue collection container 24 that allows fitting therein of fluid tube 14 or extension tube 16 to allow proper fitting and rotation.

Figure 5:
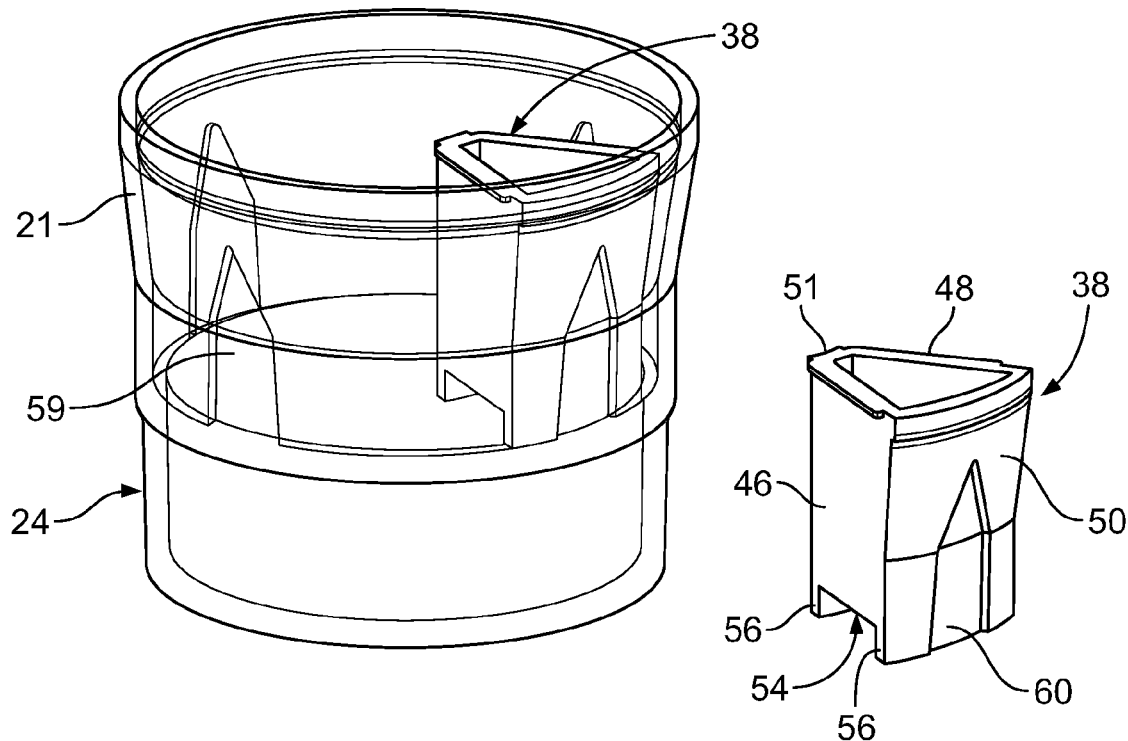
FIG. 5 shows a perspective view of the tissue collection container with one tissue collection basket inserted therein and one tissue collection basket alongside it.

As shown in FIGS. 3-5, the tissue collection 24 container contains one or more tissue collection baskets 38 removably disposed therein. Preferably, all tissue collection baskets 38 disposed within the tissue collection container 24 should be of the same dimensions and volume. Each tissue collection basket 38 comprises two substantially flat side walls 46 and 48 disposed in an angular relationship relative to each other in the manner of slices of pie or pizza, an outside arcuate wall 50 extending between the outer edges of the two side walls 46 and 48, and an inside arcuate wall 51 extending between the inner edges of the two side walls 46 and 48. The outside arcuate wall 50 of each tissue collection basket abuts the inside surface of the upper portion 24U of the cylindrical side wall 21 of the tissue collection container 24 and has a substantially cylindrical shape corresponding to the arcuate contour of outer wall 21 of the tissue collection container 24. The inside arcuate wall 51 of each tissue collection basket 38 abuts the outside surface of the annular post 32 that extends upward from the separator shelf 30 and has a substantially cylindrical shape corresponding to the cylindrical shape of annular post 32. The side walls 46,48 of each tissue collection basket 38 are oriented radially with respect to the tissue collection container 24, and the angle between the respective side walls 46, 48 of each tissue collection basket 38 depends upon the number of tissue collection baskets 38 that are fit within the tissue collection container 24.

Figure 6:
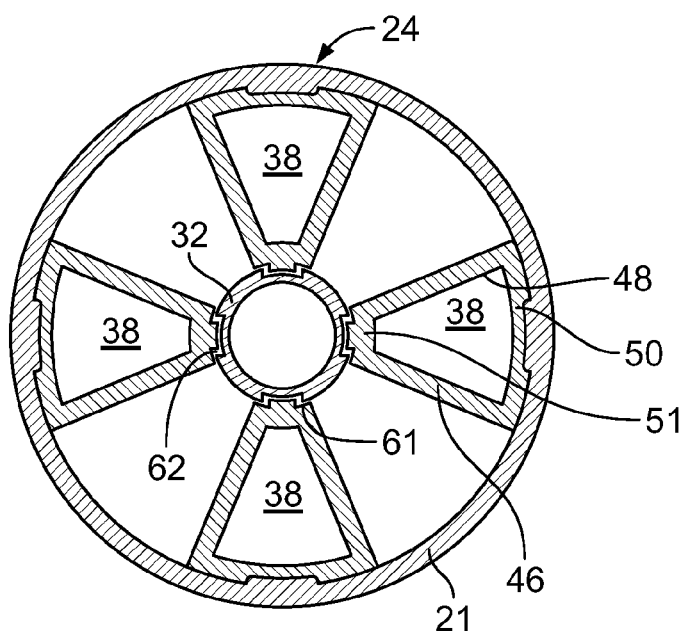
FIG. 6 shows a cross-sectional view of the upper portion of the tissue collection container along line 6-6 of FIG. 1 with four tissue collection baskets inserted therein.

Any number of tissue collection baskets 38 can be placed within the tissue collection container 24, and this number should be determined at least in part according to the volume that is needed to collect and retain a tissue sample from the body fluid. In some embodiments, as shown in FIG. 6, the tissue collection baskets 38 abut against each other, such that side wall 46 of one tissue collection basket 38 abuts against side wall 48 of an adjacent tissue collection basket 38. In some embodiments, the tissue collection baskets 38 are spaced apart from each other somewhat, such that there is a distance between side wall 46 of one tissue collection basket 38 and side wall 48 of an adjacent tissue collection basket 38. Preferably, the tissue collection baskets 38 should be evenly spaced within the tissue collection container 24. The spacing between respective tissue collection baskets 38 can be selectively chosen in accordance with desired criteria.

In one embodiment, as shown in FIG. 3 and in FIG. 6, four tissue collection baskets 38 are situated within the tissue collection container 24 in a spaced relationship. In a preferred embodiment, the cross sectional areas of the four tissue collection baskets 38 are identical, i.e., the four tissue collection baskets 38 are all of the same size, and the spacing between the respective tissue collection baskets 38 within tissue collection container 24 is also identical. In one embodiment, the cross sectional area of each tissue collection basket 38 is the same as the spacing between the respective tissue collection baskets 38.

Preferably, the side walls 46,48 of each tissue collection basket 38 extend vertically from a low position adjacent to the top surface of the separator shelf 30 to a high position adjacent the top of the tissue collection container 24, abutting the underside of the cover 26. When the cover 26 is rotated with respect to the tissue collection container 24, communication can be selected between the tissue tube 15 and one of the tissue collection baskets 38 so as to choose the tissue collection basket 38 into which the body fluid will be directed so as to enable that tissue collection basket 38 to retain a given tissue specimen that is being evacuated from the patient's body within the body fluid.

Each tissue collection basket 38 also comprises a substantially flat bottom surface 54 that extends substantially horizontally between the lower edges of the two side walls 46 and 48, the outside arcuate wall 50 and the inside arcuate wall 51. In a preferred embodiment, the lower surface 54 of each tissue collection basket 38 has holes or fluid flow apertures formed therethrough, e.g., in the form of a filter or sieve. When body fluids and tissue specimen from the patient are received in the tissue collection basket 38, the tissue collection basket lower surface 54 filters or retains the tissue specimens in that tissue collection basket 38 for subsequent removal from the tissue collection container 24. The body fluids are allowed to pass through the tissue collection basket filter holes and are collected in the lower portion of the tissue collection container 24 for subsequent removal to the fluid collection container 11 via the fluid tube 14.

When the collection and separation device 10 is properly assembled, each tissue collection basket 38 is inserted within tissue collection container 24 and supported by the separator shelf 30 which functions as a seat for the tissue collection baskets. As such, the tissue collection basket bottom surface filter 54 and the tissue collection container separator shelf 30 provide redundant separation of solid particles, e.g., tissue specimen, from body fluids passing therethrough. However, the pores through the bottom surface 54 of the tissue collection basket 38 and the filter holes in the separator shelf 30 can be formed with different pore diameters so as to provide different filtering capabilities. For example, the pores through the bottom surface 54 of the tissue collection basket 38 can be formed with a larger pore size than the filter holes in the separator 30, so that the larger tissue specimen are caught by the tissue collection baskets 38, and the smaller tissue specimen are caught by the separator shelf 30. As such, those solid particles that are not trapped by the porous bottom surface 54 of the tissue collection basket 38 and are, therefore, not retained within the tissue collection basket 38 may be retained by the filter holes in the separator shelf 30.

In order to prevent clogging of the respective filter holes of the tissue collection basket bottom surface 54 and the tissue collection container separator shelf 30, the tissue collection basket bottom surface 54 and the tissue collection container separator shelf 30 must be spaced from each other. In one embodiment, as shown in FIGS. 3 and 5, each tissue collection basket is provided with small projections 56, e.g., feet, that project or protrude in a downward direction from the bottom 54 of the tissue collection basket 38. In one embodiment, the feet 56 are provided at the corners of the tissue collection basket bottom surface 54. In another embodiment, the feet 56 are elongated along the length of the inside 51 and outside 50 arcuate walls of the tissue collection basket 38. The feet 56 raise the bottom surface 54 of the tissue collection basket 38 slightly above the separator shelf 30 so as to create a space therebetween.

In order to insure proper orientation and alignment of the tissue collection baskets 38 during assembly, the tissue specimen collection device 10 further includes a tissue collection basket positioning means to insure that each tissue collection basket 38 is properly positioned in a tissue collection basket zone, i.e., in the region of the tissue collection container 24 where the tissue collection basket 38 should be placed and not in the areas in between. The basket positioning means prevents a tissue collection basket 38 from being placed at an incorrect location within the tissue collection container 24 and allows each tissue collection basket 38 to be retained in such position once inserted by preventing it from moving or from being moved circumferentially with respect to the cylindrically-shaped tissue collection container 24.

In certain embodiments, the basket positioning means comprises a group of cooperating projections and recesses on the inside of the circumferential wall 21 of the tissue collection container 24 and on the outside arcuate walls 50 of the tissue collection baskets 38, and/or on the outer surface of the central column 32 within the tissue collection container 24 and on the inner arcuate walls 51 of the tissue collection baskets 38.

In one embodiment, as shown in FIGS. 4, 5 and 6, the basket positioning means comprises a group of projections 61 on the outer surfaces of the inner arcuate wall 51 of the tissue collection baskets 38 and a corresponding group of recesses 62 formed in the outer surface of the annular post 32 that extends upward from the separator shelf 30 towards the cover 26 of the tissue collection container 24. The outer surface of the annular post 32 that extends upward from the separator shelf 30 within the tissue collection container 24 has a slight recess 62 in its upper portion, and each tissue collection basket 38 has a corresponding projection 61 on the surface of the inner arcuate wall 51 thereof. Each projection cooperates 61 with a recess 62 to ensure that the tissue collection basket 38 is placed into, and is retained in, the tissue collection container 24 at a specific collection zone about the annular post 32. If a user is attempting to place a tissue collection basket 38 into the tissue collection container 24 at a location other than a collection zone about the central column 32, the corresponding projection 61 on the inner arcuate wall 51 of the tissue collection basket 38 will abut against the surface of the annular post 32 within the tissue collection container 24 so as to prevent the collection basket 38 from being placed downward into the tissue collection container 24 due to friction of the projection 61 abutting against the central column 32.

In another embodiment, as shown in FIGS. 3 and 5, the basket positioning means comprises a group of projections 59 on the inside surface of the arcuate wall 21 of the tissue collection container 24 and a corresponding group of recesses 60 on the outside arcuate walls 50 of the tissue collection baskets 38. Each projection 59 on the inside surface of the tissue collection container wall 21 cooperates with a recess 60 on the outside arcuate wall 50 of a tissue collection basket 38 to ensure proper alignment and retention of the tissue collection basket 38 within a collection zone of the tissue collection container 24.

In one embodiment, each projection 59 has the shape of an inverted parabola (see FIG. 3) or an inverted V or chevron (see FIG. 5), and each tissue collection basket 38 has a recess 60 with a corresponding shape of an inverted parabola or inverted V or chevron formed into the surface of the outer arcuate wall 50 thereof. In this embodiment, when a tissue collection basket 38 is placed inside the tissue collection container 24, the widest opening portion of the recess 60 on the outside arcuate wall 50 of the tissue collection basket 38 is situated over the narrowest portion (the tip) of the respective projection 59 on the inside circumferential wall 21 of the tissue collection container 24 for cooperation therewith, which allows the user's placement of the tissue collection basket 38 within the tissue collection container 24 to be inexact. Thus, when the tissue collection basket 38 is placed into the tissue collection container 24, even if inserted at a position that is slightly off from the proper collection zone position, the wide opening of recess 59 cooperates with the narrow tip of projection 60 so as to provide self-alignment of the tissue collection basket 38 within the proper collection zone position of the tissue collection container 24.

In one embodiment, the tissue specimen collection device 10 may also include an alignment indicating means to provide an indication that the cover 26 and the desired tissue collection basket 38 are aligned relative to each other. Specifically, in order to assure that the tissue inlet port 8 is in a proper position to locate a tissue collection basket 38 beneath the inserted end of tissue tube 15, alignment indicating means are provided on the tissue specimen collection device 20. Such indicating means could be a physical, structural or visual indication of whether the tissue inlet port 8 is properly aligned with respect to a tissue collection basket 38.

In one embodiment, the cover 26 could have a marking or indicia formed or placed thereon, such as an arrow or text, that indicates the position of the tissue inlet port 8 with respect to a tissue collection basket 38. In another embodiment, this indication could be provided by a structural indication formed or placed on the cover 26, such as a protrusion or arrow, that indicates the position of the tissue inlet port 8 with respect to a tissue collection basket 38. For example, as shown in FIGS. 2 and 3, cover 26 has an arrowhead that projects form the edge thereof that is radially in line with the position of the tissue inlet port 8. In another embodiment, as shown in FIG. 3, the tissue collection baskets 38 could each have indicia, such as a number or letter, printed on a visible portion thereof, such as the outside arcuate wall 50 thereof, in order to enable visual alignment of the tissue inlet port 8 with respect to the desired tissue collection basket 38.

Figure 7A:
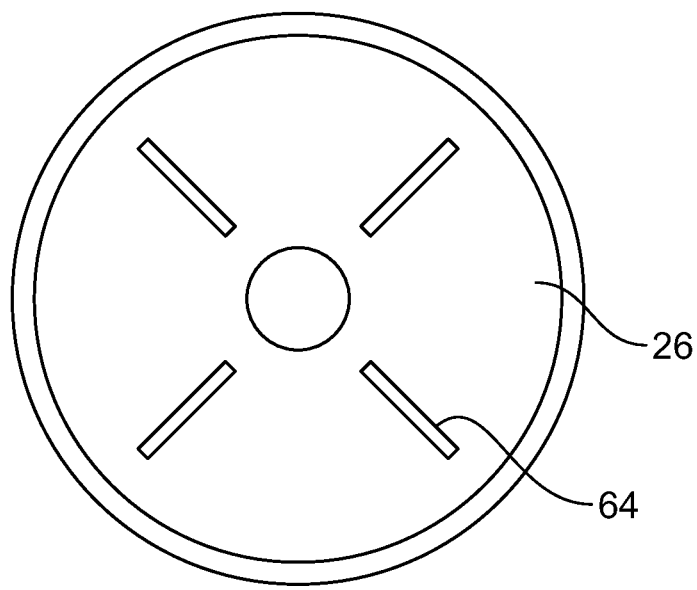
FIGS. 7A and 7B show embodiments of the tactile markings that indicates the position of the tissue inlet port with respect to a tissue collection basket.
Figure 7B:
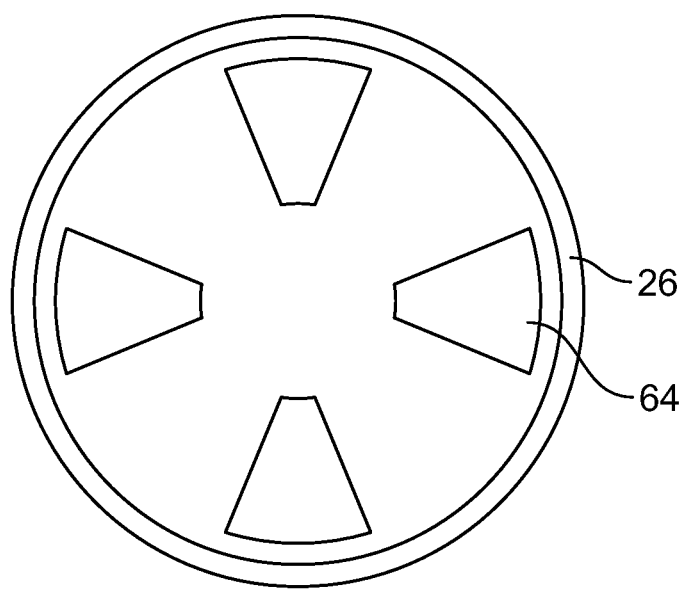

In another embodiment, the tissue specimen collection device 10 may include a tactile alignment means to provide a tactile indication that the fluid tube 15, which attaches to the tissue inlet port 8, is aligned with respect to a tissue collection basket 38 within the tissue collection container 24. In one embodiment, as shown in FIGS. 7A and 7B, the underside of the cover 26 of the tissue collection container 24 is provided with at least one projection 64 that projects downward at even a slight distance. Because the side walls 46,48 of each tissue collection basket 38 extend from a top surface of the separator shelf 28 to the top of the tissue collection container 24 and abut the underside of the cover 26, this projection 64 will rub against the upper edges of the side walls 46,48 of the tissue collection baskets 24 as the projection 64 passes thereover when the cover 26 is rotated with respect to the tissue collection container 24.

In one embodiment, as shown in FIG. 7A, this projection 64 is narrow so as to fit in between the respective side walls 46,48 of adjacent tissue collection baskets 38. In another embodiment, as shown in FIG. 7B, this projection 64 is wedge shaped so as to fit within the cross sectional area of the tissue collection baskets 38. As this projection 64 rubs against the upper edge of each side wall 46,48 of a tissue collection basket 38, it causes a bumping feeling to the user who is rotating the cover 26 with respect to the tissue collection container 24. The bumping feeling that the user feels when the projection passes over the upper edges of the side walls 46,48 of the tissue collection baskets 38 provides the user with a tactile indication of the rotation of the cover 26 with respect to the tissue collection container 24 and the position of the tissue inlet port 8 with respect to a tissue collection basket 38 as an indication of whether the tissue inlet port 8 is properly aligned with respect to the tissue collection container 24.

Of course, this tactile indication can also be supplemented by the user's visual check of whether the fluid/tissue inlet port is properly aligned with respect to a tissue collection basket by peering through the side of the tissue collection container. In a preferred embodiment, the tissue collection container is transparent to enable this visual check.

To operatively assemble the tissue specimen collection device 10, a separator shelf 30 is first positioned within the tissue collection container 24, supported by the ledge 28. The desired number of tissue collection baskets 38, each optionally bearing indicia corresponding to the number of such tissue collection baskets to be used, are positioned within the upper portion 24U of the tissue collection container 24, supported by the separator shelf 30. The tissue collection baskets 38 are situated within the collection zones, as aligned by a cooperating set of projection/recess. The cover 26 is then placed on the tissue collection container 24, and tissue tube 15 and fluid tube 14 are connected to cover 26. The distal end of tissue tube 15 is connected to an endoscope to be inserted within a patient, and the distal end of fluid tube 14 is attached to the cover 12 of the fluid collection container 11.

In order to collect tissue specimen samples from a patient's body, the user may choose which tissue collection basket 38 is to be utilized to trap the tissue specimen particles. The cover 26 of tissue collection container 24 may be rotated to align the tissue inlet port 8 with a chosen tissue collection basket 38 so as to allow body fluids and tissue from the patient to flow from the endoscope, through the tissue tube 15 and into that tissue collection basket 38 when suction is applied to the tissue specimen collection device 10.

Upon activation of the suction source or a vacuum, body fluids are removed from the lower portion 24L of tissue collection container 24 through the fluid tube 14, which preferably results in a suction condition within the tissue collection basket as well as within fluid tube 15. The suction draws specimen matter, including body fluids and solid tissue particles, from the patient's body into the endoscope and connecting tissue tube 15. The body fluids and specimen matter pass from the endoscope, through tissue tube 15 and into the upper portion 24U of tissue collection container 24 and into the desired tissue collection basket 38, and are directed towards the porous tissue collection basket bottom surface 54. The solid particles, e.g., tissue specimen, are trapped by the porous tissue collection basket bottom surface 54 and retained within the tissue collection basket 38. Those solid particles that are not trapped by the porous bottom surface 54 of the tissue collection basket 38 and are, therefore, not retained within the tissue collection basket 38, may be retained by the filter holes in the separator shelf 30. The strained body fluids pass or flow through the porous tissue collection basket bottom surface 54 and the separator shelf 30 into the lower portion of tissue collection container 24.

Body fluids collected in the lower portion 24L of tissue collection container 24 are emptied to the fluid collection container 11, and caused by suction to pass or flow through the fluid tube 14 and exit the tissue collection container 24 through fluid tube 14 to fluid collection container 11. In one embodiment, a proximal end of the fluid tube 14 itself extends into the tissue collection container 24, and the fluid can be emptied via the fluid tube 14. In another embodiment, the fluid tube 14 is attached to the tissue collection container cover 26 and is in fluid communication with the lower portion 24L thereof via the extension tube 16 that extends downward from the inside surface of the cover 24 and into the lower portion of the tissue collection container.

After collection of the tissue specimens in a first tissue collection basket 38, the cover 26 may then be rotated with respect to the tissue collection container 24 to align the tissue inlet port 8 and the tissue tube 15 with a second tissue collection basket 38 so as to allow body fluids and tissue from the patient to flow into the second tissue collection basket 38 when suction is applied to the tissue specimen collection device 10. The body fluids flow through the filter holes at the bottom 54 of the second tissue collection basket 38 and through the filter holes of the separator shelf 30 into the lower portion of the tissue collection container, while the tissue specimen are retained in the second tissue collection basket.

In one embodiment, the present invention comprises a tissue collection and separation device. Those of skill in the art will recognize that various materials of sufficient friction, flexibility, hardness and plasticity will provide the necessary functionality for the present invention.

One skilled in the art will appreciate that the present invention can be practiced by other than the described embodiments, which are presented for purposes of illustration and not limitation, and that the invention is limited only by the claims that follow. Further, since numerous modifications and changes will readily occur to those skilled in the art, it is not desired to limit the invention to the exact construction and operation shown and described, and accordingly, all suitable modifications and equivalents may be resorted to, without departing from the scope or spirit of the invention as defined in the appended claims.

We claim:

1. A collection and separation device for use in combination with a suction source to withdraw body fluids and collect tissue specimens from a patient, comprising:
    a container having an upper portion, defined by a first volume, and a lower portion, defined by a second volume;
    a lid adapted to fit onto the upper portion of the container, wherein the lid comprises a first conduit for receiving said body fluids and tissue specimens;
    a planar porous separator horizontally positioned between the upper portion and lower portions, wherein the porous separator is configured to filter and maintain the tissue specimens in the first volume while permitting said body fluids to flow into the second volume; and
    a first tissue collection basket having a plurality of sides and a horizontally planar base having a plurality of holes, said horizontally planar base configured to define a bottom of the first tissue collection basket, and at least one downward projection, wherein, when the first tissue collection basket is positioned within the first volume and on top of the porous separator, the at least one downward projection is configured to create a space between the porous separator and the horizontally planar base.

2. The collection and separation device of claim 1 wherein the container comprises an indentation extending around a circumference of the container and wherein the porous separator is adapted to rest atop said indentation.

3. The collection and separation device of claim 1 wherein the porous separator comprises annular post extending upwards toward the lid.

4. The collection and separation device of claim 3 further comprising a tube extending downward through the lid and annular post and into said second volume.

5. The collection and separation device of claim 1 wherein the lid comprises a plurality of projections extending downward into the first volume.

6. The collection and separation device of claim 1 further comprising a second tissue collection basket, a third tissue collection basket, and a fourth collection basket, wherein each of the first, second, third, and fourth collection baskets are separate and have equal dimensions.

7. The collection and separation device of claim 6 wherein each of the first tissue collection basket, second tissue collection basket, third tissue collection basket, and fourth collection basket have an arcuate cross-section.

8. The collection and separation device of claim 7 wherein the lid comprises a plurality of projections extending downward into the first volume and wherein, when the lid is turned, at least one of the plurality of projections is adapted to contact at least one side of the first tissue collection basket, second tissue collection basket, third tissue collection basket, or fourth collection basket.

9. A collection and separation device for use in combination with a suction source to withdraw body fluids and collect tissue specimens from a patient, comprising:
    a container having an upper portion, defined by a first volume, and a lower portion, defined by a second volume;
    a lid adapted to fit onto the upper portion of the container, wherein the lid comprises a first conduit for receiving said body fluids and tissue specimens;
    a planar porous separator horizontally positioned between the upper portion and lower portion, wherein the porous separator is configured to filter and maintain the tissue specimens in the first volume while permitting said body fluids to flow into the second volume;
    a first tissue collection basket having a plurality of sides and a horizontally planar base, said horizontally planar base configured to define a bottom of the first tissue collection basket, having a plurality of holes and at least one downward projection, wherein, when the first tissue collection basket is positioned within the first volume and on top of the porous separator, the at least one downward projection creates a space between the porous separator and the horizontally planar base;
    an annular post extending upwards from the porous separator toward the lid; and
    a tube extending downward through the lid and annular post and into said second volume.

* * * * *